United States Patent [19]

Jaeger et al.

[11] 3,973,001

[45] Aug. 3, 1976

[54] TISSUE CELL STIMULATING BLOOD EXTRACTS

[75] Inventors: Karl-Heinz Jaeger, Freiburg; Hellmut Mittenzwei, Munich, both of Germany

[73] Assignee: Solco Basel AG, Birsfelden, Switzerland

[22] Filed: Jan. 22, 1975

[21] Appl. No.: 542,910

Related U.S. Application Data

[63] Continuation of Ser. No. 828,440, May 22, 1969, abandoned, which is a continuation of Ser. No. 349,785, Feb. 12, 1964, abandoned, which is a continuation-in-part of Ser. Nos. 503,344, April 22, 1955, abandoned, and Ser. No. 627,242, Dec. 10, 1956, abandoned.

[30] Foreign Application Priority Data

Apr. 27, 1954 Germany...................... 1017744

[52] U.S. Cl............................ 424/101; 260/112 B; 424/177
[51] Int. Cl.² .................. A61K 35/14; A61K 37/00
[58] Field of Search ........... 424/101, 105, 177, 195; 260/112 R, 112 B

[56] References Cited

UNITED STATES PATENTS

| | | | |
|---|---|---|---|
| 2,239,345 | 4/1941 | Sperti................................. | 424/105 |
| 2,320,479 | 6/1943 | Sperti................................. | 424/195 |
| 2,433,879 | 6/1948 | Wretlind............................. | 424/177 |
| 2,554,632 | 5/1951 | Nessett............................... | 424/177 |

*Primary Examiner*—James O. Thomas, Jr.
*Assistant Examiner*—A. P. Fagelson
*Attorney, Agent, or Firm*—Hammond & Littell

[57] ABSTRACT

Novel blood extracts of vertebrata, i.e. animals having a vertebral column, especially warm blooded animals, which blood extracts possess cell respiration stimulating activity and stimulate the growth of cells and to novel processes for the preparation of the said blood extracts.

8 Claims, No Drawings

TISSUE CELL STIMULATING BLOOD EXTRACTS

PRIOR APPLICATIONS

This application is a continuation of U.S. application Ser. No. 828,440 filed May 22, 1969, now abandoned, which is a continuation of application Ser. No. 349,785 filed Feb. 12, 1964, now abandoned, which is a continuation-in-part application of U.S. Pat. applications Ser. No. 503,344 filed Apr. 22, 1955 and Ser. No. 627,242 filed Dec. 10, 1956 both now abandoned.

PRIOR ART

Blood and blood serum (the liquid portion of blood with the corpuscles removed) have often been used for therapeutic purposes. For example, blood transfusions from one person to another have been performed and blood from "bloodbanks" has been employed in many circumstances. Also, blood has been removed from patients and irradiated, preferably with ultraviolet light, and then reinjected into the patient.

In so-call stimulant therapy, animal blood has been used for external and internal application such as serum therapy in infectious diseases, the use of individual blood protein fractions such as gammaglobulin or antihaemophilic globulins (AHG) in haemorrhages, the use of Bogomoletz serum, of so-call regenerating sera, etc. Blood or serum has also been used for the recovery of hormones since frequently the hormones are present in larger quantities in the blood than in the organs and they can be more easily extracted and recovered in pure form from blood. For example, gonadotropic hormones are frequently obtained from the serum of pregnant mares.

Attempts have been made to find other hormone-like substances in the blood, particularly substances which have a regenerative action on tissue undergoing degenerative processes but which are not found in the cells or tissue. However, it is extraordinarily difficult to identify and isolate from blood substances with regenerative activity on tissue undergoing degenerative processes or chronical inflammatory processes since a large number of substances which possess functions which mutually counteract or overlap are present in blood.

It is an object of the invention to provide novel blood extracts of vertebrata, especially warm blooded animals, which possess cell respiration stimulating activity.

It is another object of the invention to provide novel processes for the preparation of blood extracts of vertebrata, warm blooded animals, which possess cell respiration stimulating activity.

It is a further object of the invention to provide a novel method for stimulating the growth of tissue undergoing a degenerative process.

These and other objects and advantages of the invention will become obvious from the following detailed description.

The novel blood extracts from vertebrata, especially warm blooded animals, of the invention are (a) protein free extracts containing about 25 to 75 percent by weight of inorganic components and about 75 to 25 percent by weight of organic components whose molecular weights do not exceed 2500-3500 (b) have the following identifiable components: phosphorus, chlorine, nitrogen, sulfur, carbonate ($CO_2$), sodium, potassium, calcium, magnesium, iron, copper, silicon, manganese, aluminum, glucose, other hexoses, other reducing substances, glucosamine, urea, uric acid, kreatin, kreatinin, amino acids, peptides, glutathion, AMP, $\alpha$-ketoglutaric acid, pyruvic acid, lactic acid, malic acid, fructosediphosphate, $\alpha$-glycerolphosphate, dihydroxyacetonphosphate, adenosinediphosphate (ADP), glucose-6-phosphate, phosphoserine, phosphoethanolamine and cholesterin (c) give a negative sulfosalicylic acid and trichlorosalicyclic acid reaction for protein, (d) give a positive glucose test, ninhydrin reaction and Millon's reaction and (e) have a cell respiration activity increase of at least 100 percent over a control as determined by the Warburg et al method on homogenates and mitochondria.

The blood of vertebrata which is used to obtain the blood extract of the invention is the blood of sexually immature animals or the blood of animals which have been placed in a condition of changed activity by chemical treatment or by irradiation. Instead of using the whole blood of the said animals, the blood cells and the plasma may be separated and treated individually since the respiration stimulating active substance is contained in the blood cells and the plasma. Blood cells of calves is an extraordinarily cheap starting material because slaughter houses have no use for it.

The blood of very young animals such as about one month old calves has a high percentage of the respiration stimulating component but this decreases with the age of the animals. Since animals are not normally slaughtered at this age in many regions, it may be advantageous for commercial reasons to subject the said animals to one of the following treatments to increase the concentration of the respiration stimulating component in the blood of the animals before slaughtering.

The pretreatment of the animals, particularly calves, may be effected either by administering to them one or more of the chemical compounds defined below or by subjecting them to irradiation. This treatment increases the concentration of respiration stimulating component in the blood and thereby the isolation thereof will be facilitated.

The amount of chemical stimulation or irradiation necessary to produce the desired respiration stimulating activity can be determined by preliminary tests. The amounts of roentgen (R) needed to stimulate an organ (stimulating irradiation) is known and therefore, it is possible to adjust the desired stimulation depending upon the type of irradiation. The dosage of the chemical treatment or the irradiation should be below that which causes irreparable damage to the organ and possible death of the animal. These dosages are well known to those skilled in the art and can be obtained from many texts in this field.

Any type of irradiation is suitable which stimulates either the entire body or organs such as skin, spleen, bone marrow, kidneys, etc. Examples of suitable types of irradiation are very short radium radiation, longwave, middlewave or shortwave X-ray radiation, grenz ray radiation (Bucky rays), ultraviolet light, infra-red, longwave heat radiation, corpuscular ray radiation such as by canal rays, rapidly moving electrons, positrons, neutrons and similar elementary particles or particles derived from radioactive isotopes. Ultrasonic waves may also be used for stimulation. Irradiation has the great advantage that it is possible to focus most types of rays to the specific part of the body to be treated and to concentrate the said rays upon a specific plane of the animal's body.

The chemical stimulants are preferably hypotonic aqueous solutions which produce a partial hemolysis when injected intravenously into the animal. Examples of suitable solvents are distilled water or hypotonic solutions whose ion concentrations may be between zero and a value which still causes hemolysis in the animal.

Examples of suitable chemical stimulants are salts which in aqueous solution form ions such as sodium chloride sodium phosphate, sodium sulfate, other buffer compounds, dispersed substances which in the organism will not be removed in urine but will be stored in the Reticulo-endothelial system (RES) such as colloidal sulfur and india ink, dyestuffs particularly biologically active dyestuffs having a specific range of fluorescence such as methylene blue, eosine, trypan red, trypan blue, porphyrine, etc. and therapeutically active compounds such as phenol derivatives, benzoic acid derivatives such as the methylate of p-hydroxybenzoic acid and p-amino-benzene and hemolytically active substances such as saponins. Radioactive elements and compounds such as radioactive cobalt, iodine or phosphorus may also be used as chemical stimulants but are preferably used as indicators for the chemical stimulants mentioned.

The process of the invention for the preparation of respiration stimulating extracts from blood of warm blooded animals comprises (1) recovering the blood of animals selected from the group consisting of sexually immature warm blooded animals such as calves less than 8 or ten weeks old, warm blooded animals which have been subjected to irradiation and warm blooded animals which have received intravenous injections of hypotonic aqueous solutions (2) defibrinating the said blood, (3) subjecting the defibrinated blood to hemolysis, (4) fractionally precipitating proteins from the hemolyzed blood solution and (5) concentrating the resulting protein-free solution to a concentration of 10 to 60 mg of dry components per ml. The respiration stimulating extracts obtained thereby are suitable for topical applications to the skin as in salves or intramuscular injections after sterilization.

If the respiration stimulating extracts are to be administered intravenously, the deproteination step is preferably replaced with a dialysis step since irritation occasionaly occurs with the extracts obtained by protein precipitation when administered intravenously. The hemolyzed blood is subjected to dialysis with a membrane adapted to pass compounds having a molecular weight up to 4500 to remove proteins, high molecular weight blood constituents and protein degradation products and the outer dialysate is fractionally concentrated to a concentration of 10 to 60 mg of dry components per ml of solution. After sterilization, the resulting solution of the blood extract can be administered intravenously directly or intramuscularly after making the solution of extract isotonic.

The defibrination of the blood is preferably effected by mere stirring of the blood which changes the fibrinogen to fibrin due to the presence of peptic substances in the blood particularly thrombine. When the blood has separated into a solid fibrin phase and a liquid phase of erythrocites in serum, the stirring is stopped and the two phases are separated by filtration or decantation and the solid phase is discarded. The defibrination can also be effected by peptic digestion of the blood with pepsin at a pH of 2 to 3 or by tryptic digestion of the blood with trypsin at a pH of 8 to 9. In the latter case, a partial deproteination accompanies the defibrination.

Hemolysis of the defibrinated solution which is the destruction of red blood corpuscles is effected by mixing the said solution with water, preferably an equal volume of water and solution, which causes the cell membranes to be destroyed by the change in osmotic pressure. Hemolysis occurs after a few hours but it is preferred to let the solution stand for a few days, i.e. 5 to 7 days, at 0°C. to complete the hemolysis and to partially destroy proteinaceous material which aids in separating the respiration stimulating components from the proteins. The insoluble material is separated from the hemolyzed solution by filtration or centrifugation.

The fractional deproteination of the solution may be effected by known means such as by precipitation by the stepwise addition of low molecular aliphatic alcohols, organic or inorganicc acids or salts thereof. Examples of suitable alcohols are methanol, ethanol, isopropanol, etc. Perchloric acid is a preferred acid for the protein precipitation since it is easily removed by treatment with alcoholic solution of soluble potassium compounds which do not have interfering anions such as potassium hydroxide which forms potassium perchlorate. Trichloroacetic acid may also be used but its removal by extraction with ether also extracts a portion of the respiration stimulating activity.

The dialysis to remove components having a molecular weight greater than 4500 is preferably effected at low temperatures of the order of 2°C. using water or dilute alcohols such as 10 percent aqueous ethanol as the dialysis media. Cellophane tubes have been found to be particularly suitable as the dialysing material although other dialysis materials may be used. The dialysis treatment may be repeated several times until the last outer dialysate fraction obtained is free of organically bound nitrogen. If desired, the hemolyzed blood solution can be subjected to a partial deproteination as described above.

The outer dialysates are combined and the pH of the resulting solution is adjusted to about 7 and if necessary the solution is filtered to remove any salts that may precipitate. The solution is then concentrated fractionally in vacuo at temperatures not above 30°C., i.e. 20°–25°C., until cloudiness appears to remove all alcohol and the solution is filtered, and the process is repeated until the solution contains 10 to 60 mg of solids per ml of solution.

The concentrated solution obtained by concentration of the dialysates can be administered after sterile filtration by any means except by intramuscular injections. This is due to the fact that the solution is three times hypertonic due to the presence of salts. The said solution can be further purified for intramuscular injections by additional steps.

One method comprises adding low molecular weight aliphatic ketones or alcohols to the dialysate concentrate to obtain a moderate precipitate showing a small part of the active substance. After removal of the precipitate by filtration, the solvent may be concentrated in vacuo to completely remove the low molecular solvent and can then be filtered under sterile conditions. Acetone is a particularly useful low molecular aliphatic ketone.

A more preferred purification method comprises shaking or stirring the dialysate concentrate with a water-immiscible or partially water miscible solvent such as an aliphatic alcohol having 3 to 8 carbon atoms, i.e. butanol, to obtain a two phase system and separating the two phases. The majority of the undesired salts remain in the aqueous phase and most of the respiration stimulating substance (about 60 percent) is in the butanol phase. The organic solvent is removed by vacuum distillation and the dry residue is dissolved in water to obtain the desired concentration which aqueous solution is about hypotonic. The aqueous phase which contains about 40 percent of the respiration stimulating components may be concentrated and used for topical applications such as in ointments.

Another method comprises evaporating the dialysate concentrate or the fractions obtained by the above purification operations to dryness, taking up the residue with distilled water and subjecting the resulting solution to sterile filtration and, if desired, to lyophilize it under sterile conditions.

The blood extracts of the invention are stable and can be stored for prolonged periods of time of at least 3 years without suffering any loss of activity. However, if desired, a preservative such as phenol, cresol, etc., may be added. Preservatives to prevent a secondary infection of the solution after opening of the container in which it is supplied may also be added.

The respiration stimulating substances of the blood extract have a low molecular weight not greater than 3500. The new active substances differ fundamentally from known substances conveyed from the blood or obtained therefrom. In tests in the Warburg apparatus the said substances produce a respiration increase of 100-400 percent in tissue homogenates which is not exclusively substrate depending. The increased oxygen uptake does not result in a decrease of the phosphorus-oxygen quotient which means that the increased oxygen uptake results in a proportionate increase of organic phosphates rich in energy in the cells. This degree of respiration increase cannot be achieved with any known substances thus far isolated from blood.

The novel blood extracts of the invention are useful for the treatment of ulcerations of the gastrointestinal tract or of the skin, myocardiac infarct, angiopathies due to the blood circulation disturbances, metabolism disturbances, sclerosis and disturbances in healing processes of the skeleton, for instance after bone fractures. Particular success has been had in treating trophic ulcers such as X-ray ulcerations which have been previously considered to be incurable by the administration of conventional drugs, but which have been completely cured with the blood extract of the invention.

In the following examples there are described several preferred embodiments to illustrate the invention. However, it should be understood that the invention is not intended to be limited to the specific embodiments.

EXAMPLE I

The kidneys of a healthy young cow three months old and weighing about 60 kg were irradiated by means of deep X-ray radiation in scattered doses of at least 3000 roentgens in which an aluminum sheet of 1 mm thickness and a voltage of 120 Kv were used. As soon as tests of the catheter urine originating from the irradiated kidneys showed that the kidneys had started to function again, the kidneys were operatively exposed and a puncturing needle was introduced into and tied up to the renal veins. 2 liters of blood (about 40 percent of the amount of circulating blood of the treated animal) was withdrawn from the said veins and was extracted according to the following process.

The freshly withdrawn blood was subjected to hemolysis and was freed from protein by adding trichloroacetic acid thereto to precipitate the proteins. The protein free liquid was then subjected to a peptic-tryptic fermentation process at a pH of 2.0-9.0 and a temperature of about 37°C. to set free the active compounds contained therein. The resulting liquid was again treated with trichloroacetic acid to remove proteins freed in the fermentation process and was then concentrated by evaporation to about one-half to one-quarter of its original volume. After adding five volumes of anhydrous acetone thereto, the resulting precipitate was removed from the liquid by centrifuging.

The precipitate was extracted with ether or chloroform and the extract was freed from fatty acids, cholesterol and other accompanying substances and the dark yellow active residue when dissolved in olive oil formed a solution suitable for intramuscular injection.

The residue from the acetone precipitation was extracted several times with an isotonic sodium chloride solution at a pH between 5.0 and 7.0 and the combined extracts were freed from protein by fractional precipitation of protein by the addition of ethanol. The solution was then subjected to freeze drying and the dried material could be directly used for preparing an isotonic injection solution or could be dissolved in water and the aqueous solution subjected to dialysis. The external dialysate could be directly used and is characterized by a maximum absorption band at 260 millimicrons.

EXAMPLE II

One liter of blood of calves about six weeks old which was freshly withdrawn after slaughtering was admixed with one liter of distilled water whereby hemolysis occurred. The fibrin residue was removed from the resulting solution by coarse filtration.

The two liters of solution was then adjusted to a pH of 8 and was partially digested with 0.2 gm of highly purified trypsin for 24 hours at 37°C. After adjusting the pH of the resulting solution to 7, six liters of acetone were added to the solution to effect a quantitative precipitation. The precipitate is recovered, stirred with 2 more liters of acetone and then with two liters of a 50 percent acetone—50 percent ether mixture, sharply centrifuged and dried to 300 to 320 gm of dry product.

The dried product was then stirred with 4 to 5 parts of distilled water and the resulting suspension was dialysed at about 2°C. against the same amount of water using a cellophane tube. The dialysis treatment was repeated until no appreciable amount of organically bound nitrogen migrated into the outer dialysate. The outer dialysates were combined and concentrated in vacuo at a temperature of 20°-25°C. to a volume of 200 ml. The dry weight of the resulting solution was about 36 mgm/ml. After sterile filtration and the addition of a preservative such as phenol or cresol, the solution was suitable for therapeutic application.

The solution which had a high respiration-enhancing activity contained the degradation products of nucleic acids, amino acids and oligopeptides which can be characterized by paper chromatography or paper electrophoresis.

EXAMPLE III

To 500 ml of fresh calves blood which has been defibrinated by stirring, 500 ml of distilled water were added. After standing at room temperature for 24 hours the clear solution was separated from any suspended material. To the clear solution 2000 ml of 96 percent ethyl alcohol were slowly added with stirring over a period of 1 hour while maintaining the temperature at ±2°C. The stirring was continued for five hours and the alcoholic solution was separated from the precipitate by centrifuging. The alcoholic solution was filtered and concentrated in vacuo at a maximum temperature of 22°C. to 100 ml of an alcohol-free concentrate. After the pH of the concentrate was adjusted to 7, approximately 400 ml of alcohol were slowly added to the concentrated solution while stirring in the cold to bring the solution to a concentration of 80 percent by weight of alcohol and the resulting solution was allowed to stand for 24 hours at 0°C. The protein precipitate formed contains practically no respirationenhancing activity and was discarded. The alcohol solution was again concentrated in vacuo to 100 ml until it was free from alcohol and was then filtered under sterile conditions. The solution which contained 15 mgm of dry substance per ml and which had a freezing point depression of 1.18°C. could be used directly for therapeutic purposes.

EXAMPLE IV 200 ml of blood freshly withdrawn during slaughtering of a 6 weeks old calf was defibrinated at room temperature by stirring with a wooden stick (about 10–30 minutes depending upon temperature and time during which the blood has been standing) to transform the fibrinogen contained in the blood into fibrin. The stirring was discontinued when the blood divided into a liquid phase, that is, a decantable suspension of erythrocytes in the serum, and a solid phase. The liquid phase was decanted from the solid phase which was the high molecular weight fibrin.

The defibrinated blood thus obtained was admixed with an equal amount of distilled water and was allowed to stand at 0°C. for a few days. Durin this time, a hemolysis of the red blood corpuscles and a slight proteolysis of the proteins contained in the blood took place. The deep red blood solution thus obtained was filtered or centrifuged until clear and was dropwisedly admixed in the cold with 18 ml of a 60% perchloric acid solution accompanied by vigorous stirring. The proteins were denatured by the perchloric acid and were precipitated from the solution. The precipitation was complete as soon as the perchloric acid concentration in the overall solution was 0.4–0.6 normal. In order to avoid inclusions of respiration-active substances in the protein precipitate, the perchloric acid had to be added very slowly over the course of 2–3 hours. Then the mixture was stirred for an additional hour in the cold. The protein precipitate was centrifuged off and was washed with a small amount of 0.4 normal perchloric acid solution.

The filtrate and the wash solution were combined, again filtered until clear and admixed at 4°C. with about 40 ml of 5 normal KOH until a pH value of 7.2–7.3 was reached to precipitate potassium perchlorate. By addition of absolute alcohol in an amount of about 50 percent of the volume of the suspension, the potassium perchlorate precipitation was brought to completion and after allowing the mixture to stand at 0°C. for 24 hours, the liquid portion was centrifuged or filtered off from the potassium perchlorate.

The clear yellow solution thus obtained was concentrated in vacuo at a temperature which did not exceed 25°C. to evaporate all the alcohol therefrom. 175 ml of a protein-free active substance solution with a content of dry substance of 17.4 mgm/ml and a freezing point depression of 1.6°C. was obtained. This solution could be filled into ampules and after addition of an approved preservative such as phenol used for injection purposes.

EXAMPLE V 1 liter of fresh blood, which was withdrawn immediately after slaughtering of a 6 week old calf, was stirred at room temperature in order to transform the fibrinogens into fibrin. The fibrin thereby separated in compact threads on the stirrer and on the walls of the container. The residual blood, a suspension of erythrocytes in serum, was then readily decanted from the solid fibrin material. The liquid phase which was the defibrinated blood was admixed with an equal amount of distilled water, whereby hemolysis sets in. Hemolysis is the destruction of the red blood corpuscles due to the change of the osmotic pressure in the cells. Hemolysis occurred after only a few hours. However, it has been found to be advantageous to allow the above-described blood solution diluted with water to stand for about 6 days at 0°C. During that time the hemolysis has gone to completion and the protein-splitting ferment contained in the blood, such as the endopeptides, are activated and lead to an easy alteration of the blood proteins, whereby the active substance of the present invention are set free. After 6 days the solution was centrifuged, whereby additional insoluble substances, such as residual fibrins, erythrocyte ghosts, membranes, etc. were separated and a clear deep red solution was obtained.

About 2000 ml of the deep red solution were then placed at 2°–4°C. into a cellophane tube with a permeability for molecules with a molecular weight of up to about 3500 and the solution was dialyzed against an equal volume of distilled water. In place of the distilled water, a 10 percent aqueous ethanol solution is advantageous in two respects: (1) sterile conditions are obtained thereby, and (2) the dialysis proceeds somewhat more rapidly. The dialysis treatment was repeated several times until no substantial amount of nitrogen (determined according to Kjeldahl) migrated into the outside dialysate. After combination of the individual outside dialysate portions, about 8000–10,000 ml of outside dialysate solution were obtained. This solution was concentrated in vacuo at a temperature of not over 25°C. until the solution became cloudy. The cloudy solution (about 500 ml) was allowed to stand for 24 hours in the cold and then the inactive precipitate was removed by filtration.

The pH of the filtrate was between 8.0 and 9.0 and was adjusted to a pH of 7.0 with dilute hydrochloric acid. Dilute phosphoric acid may also be used for the neutralization with good results. The neutral solution was again concentrated in vacuo, to about 100 ml, whereby cloudiness was again formed. The cloudy solution was again allowed to stand for 24 hours and was then filtered and the inactive precipitate was discarded. The pH of this solution was again adjusted to 7.0, as above and the dry weight was determined. The solution was diluted or concentrated to a concentration of 40 mgm/ml of dry substance.

All operations are performed under sterile conditions because bacterial impurities lead to a more or less extensive desruction of the active substances.

The solution thus obtained had a high respiration-promoting activity. In comparison to the controlled respiration of mitochondria or liver homogenate from about 100 mgm of fresh rat or guinea pig liver, the addition of 0.2 ml of this solution produced in the Warburg apparatus an increase of over 200 percent of the oxygen absorption. The ultraviolet absorption curve of the neutral dilute solution exhibits maxima at 205, 245 and 290 m$\mu$ and a minimum at 230 m$\mu$. In hydrochloric acid solution, a maximum was observed at 280 m$\mu$ and a minimum at 250 m$\mu$. The paper chromatographic analysis shows that the extract contains nucleic acid derivatives, amino acids and peptides.

The solution obtained above was filled into ampules after addition of a preservative and sterile filtration. The contents of the ampules were suitable for intravenous injection.

The solution was hypertonic (the freezing point depression lies between 2.0° and 2.6°C.) and was therefore less suitable for intramuscular injection. A somewhat isotonic solution with a freezing point depression of 0.5°–0.7°C. was obtained by extraction of the said solution with aqueous butanol. 100 cc of the concentrate with a dry weight of 40 mgm/ml were adjusted with hydrochloric acid to a pH of 4.5 and were extracted three times with 50 cc portions of butanol saturated with water (about 5–7 percent water, depending upon the temperature). The major amount of inorganic salts remained in the aqueous phase and the butanol phase was evaporated to dryness in vacuo. The dry substance was dissolved in 50 cc of distilled water and the solution was again adjusted with dilute sodium hydroxide with a pH of 7.0. This solution had a dry weight of 10–15 mgm/ml and contained about 60 percent of the original respiration-active substances. This solution was preferably used for intramuscular injection. The aqueous phase still contained about 40 percent of the respiration-active substance and could be used for local external application, for instance, in ointments.

By means the extraction with n-butanol saturated with water, the ratio of inorganic components to organic components was displaced in favor of the latter. While the hypertonic solution of the active substance of the present invention has a ratio of inorganic to organic components of about 75:25, this ratio in isotonic solutions suitable for intramuscular injection lies at about 25:75. Depending upon the extent to which the butanol extraction is carried out, solutions with corresponding intermediate ratios of inorganic to organic components may be obtained.

PHARMACOLOGICAL DATA

I. Methylene blue test of Respiration Activity 1 ml of methylene blue solution (1:5000) was decolorized with 1 ml of freshly prepared sodium dithionite ($Na_2S_2O_4$) solution (1:100). After 0.5 ml of a physiological sodium chloride solution was added to the decolorized solution as a blind value, a metered stream of oxygen was passed through the solution by means of a glass capillary. The solution turned blue due to oxidation in 30 minutes. The test was repeated except that 0.5 ml of the solution of example V was added instead of the sodium chloride solution and the solution turned blue after only one and a half minutes which demonstrates the catalytic respiration-stimulating activity of the blood extract of the invention. Other organic extracts were substantially less active requiring 5 to 30 minutes to oxidize the solution to methylene blue.

II. Increase in Metabolism of Brain Cells

The metabolism of the brain cells depends upon a sufficient supply of oxygen and all functions of the brain essential for life are connected therewith. An insufficient supply of oxygen can be visualized objectively in the electroencephalogram (EEG) because the brain currents drop off when there is insufficient supply of oxygen to the brain.

When anesthesized rats are transferred in a pneumatic cage to an equivalent altitude of 8700 meters (corresponding to a vacuum of 241 mm Hg), the brain currents in the EEg disappear, which is a sign that an insufficient supply of oxygen for production of the energy demanded is present. When the same test animals are injected with 25 ml of the active substance solution prepared in example V (40 mgm dry substance per ml) per kgm of body weight 20 minutes prior to transposition to 8700 meters, the brain currents are sustained even at an altitude of 8700 meters, which shows that the brain cell remains fully capable of functioning despite the reduced oxygen pressure in the blood due to respiration-stimulating activity of the blood extract of the invention. This effect is useful in clinical therapeutic application for sclerosis of the brain.

III. Increase in Oxygen Consumption — Warburg Test

FIG. 1 illustrates the effect of the blood extract of the invention on the respiration of total liver homogenate. The measurements were taken in a Warburg apparatus at 37°C. and the oxygen consumption was followed manometrically in its temporal course. The rat liver homogenate of 1:4 was produced with a Sorensen buffer having a pH of 7.4 and 0.2 ml of the blood extract with a Sorensen buffer adjusted to a pH of 7.4 was added. The tempering time was 10 minutes and the frequency of shaking beats was 10 per minute.

In FIG. 1 the ordinate represents the oxygen consumption expressed in $mm^3O_2$ and the abscissa represents the test time expressed in minutes. x-x-x represents the test using rat liver homogenate alone, o-o-o represents the test for rat liver homogenate and 0.2 ml of the extract of the invention. As can be seen from FIG. 1, the blood extract of the invention gives a 400 percent respiration increase after 50 minutes. The results can be reproduced with the usual biological margin of error of ± 10 percent.

Up to now, the biological oxidation of adrenaline has been ascribed to certain enzymes such as aminooxydases and polyphenoloxydases. Adrenaline has been found to be catalytically oxidized by the blood extract of the invention without the aid of any enzyme and this characteristic property is useful for testing the activity of the blood extract of the invention. The measurements of this characteristic property may be effected by the manometric Warburg method using shaking vessels containing 0.4 ml of 1N NaOH in aqueous solution in the auxiliary receptacle and 0.2 to 0.4 ml of the blood extract and 0.6 ml of a 200 mg % solution of adrenaline bitartrate in the reaction zone at a temperature of 38°C. and a frequency of shaking beats of 80 to 100 per minute. Oxygen is passed over the manometric system for 10 minutes while maintaining the temperature of 38°C., then the oxygen comsumption was recorded every 10 to 20 minutes. The results are summarized in Table I.

TABLE I

| | Oxygen Consumption in mm³ after | |
|---|---|---|
| | 1 hour | 2 hours |
| Blood extract | 7.1 | 9.8 |
| Adrenaline solution | 1.4 | 3.9 |
| Adrenaline solution and blood extract | 134.2 | 172.8 |

As can be seen from table I, a direct proportionality exists between the oxygen consumption and the respiration stimulating activity of the blood extract of the invention.

IV Clinical Study in Chronic and Acute Skin Ulcers

Over a period of 5 years, the product produced by the process of example V was studied for its effect on different skin diseases. A total of 62 cases were studied in which the cases had not responded to other treatments. As a rule, 2 ampules (4 cc) of the blood extract were administered daily but in particularly severe cases, 4 ampules were administered daily. No side effects were observed and tolerance of the injections was optimal. Combination with antibiotics or sulfonamides when necessary was possible without difficulty. A 5 percent ointment was a valuable complement to the parental treatment and it was well tolerated. In small ulcers, local treatment along was sufficient whereas a combination of injections and local treatment was used in the more serious cases. The results are summarized in Table II.

TABLE II

| Diagnosis | Number of Cases Treated | RESULTS | | |
|---|---|---|---|---|
| | | Very Good | Good | No Result |
| Ulceracruris permagna | 36 | 21 | 5 | 10 |
| Chronic X-ray ulcers | 18 | 8 | 4 | 0 |
| Acute X-ray ulcers | 6 | 6 | 0 | 0 |
| Decubital and trophic ulcers | 8 | 4 | 2 | 2 |

The results of Table II show that the blood extract of the invention gives good results in 80 percent of the cases treated, which cases were extremely difficult.

V. Accelerations of Healing in Maxillary and Facial Surgery

Ninety operative cases of facial and maxillary surgery were treated locally and parenterally with blood extracts produced by the process of example V. Accelerated healing and formation of better structurized scars occurred in plastic surgery and bone fractures became clinically and roentgenologically consolidated in less time when the blood extract was administered parenterally. In surgery, intravenous administration of the blood extract is preferred to intramuscular administration or the two methods of administration should be alternated. In surgery involving tissue grafts, pretreatment with the blood extract is desirable.

Local application of the blood extract in the forms of a jelly or ointment in bone cysts and open wounds of tissue speeds healing per secudum and the healing is more regular, markedly accelerated and leaves a scar which is optimum in structure and resistance to stress. No side effects or allergic reactions due to the blood extract occurred.

VI: Treatment of Trophic Ulceration of Foot in Leper

Blood extracts produced by the process of example V were administered to seven lepers having ulcerations of the foot. The results are summarized in Table III.

TABLE III

| Age | Sex | Type and Duration of Ulcer | Complications | Dosage | Result |
|---|---|---|---|---|---|
| 30 | M | Tb. 6 yrs. | Nil | 2 ml daily for 18 days | healed |
| 22 | M | Tb. 1 yr. | Osteomyelitis and bone destruction | idem | no improvement |
| 50 | M | Tb. 10 yrs. | idem | idem | idem |
| 17 | F | Tb. 6 yrs. | Osteoporosis and Absorption of 2nd, 3rd, 4th and 5th metatarsal bones | 2 ml daily for 36 days | idem |
| 46 | F | Tb. 2 yrs. | Nil | 2 ml daily for 18 days | healed |
| 29 | F | Tb. 3 yrs. | Nil | idem | healed |
| 30 | F | Tb. 6 yrs. | Main-en-griffe with clawfoot — Ulcer of tips of toes and fingers with destruction of distal phalanx | idem | healed |

All cases uncomplicated with osteomyelitis or osteoporosis healed completely after a minimal course of 18 injections. No side effects were observed during the course of the treatment.

VIII: Clinical Treatment of Gastric and Duodenal Ulcers 40 cases of intestinal ulcers of which 16 were ambulatory and 24 were hospitalized were treated with the blood extract produced by the process of example V. All the hospitalized patients were put on a pepetic ulcer diet. Otherwise, diet was largely assimilated to normal meals except that food promoting gastric acidity was avoided. Several patients who were admitted to the hospital with the symptoms of an ulcer crisis had to be administered antacids and antispasmodics. To ambulatory patients we recommended abstinence from alcohol, nicotine, coffee and strongly spiced dishes, else no special diet was prescribed. (It was ascertained later that these recommendations were not generally followed, particularly the order not to smoke was frequently infringed). The patients were given varying therapeutic doses of the blood extract depending on their clinical and roentgenological status. Injections of 2-4 cc of the blood extract over 4 to 20 days (10 days on an average) were administered to 31 patients intravenously and to 9 patients intramuscularly. In no case side effects were observed. The final X-ray examination was done between the 10th and the 40th day (on the 19th on an average). Out of a number of 24 patients with direct evidence of ulcer there was complete disappearance in 17 cases while in 7 cases X-rays showed cicatrization. In the cases of indirect diagnoses the signs of ulcer had disappeared 8 times completely while in the remaining 8 cases they were traceable as bulb deformities — mostly diminished in size — depite the clinical criteria of healing. This factor of uncertainty in judging the healing of a duodenal ulcer is practically not avoidable, therefore, the clinical state must be taken as a criterion in judging the success of a treatment. According to observation made so far no ulcer was detectable in any case after treatment with the blood extract. In the majority of cases patients were free of complaints after a few injections (5 on an average). The general condition improved strikingly, a fact which was also clearly expressed in the increase in weight which in some cases continued remarkably also after treatment. One patient had a relapse 5 months after treatment which — according to the patient's confession — was obviously due to abusive consumption of nicotine and coffee together with a very irregular way of living (truck driver). In this case a repetition of the treatment brought about a remission within a few days.

For the 40 cases, the blood extract of the invention proved to have a constant effect and to have a rapid efficacy, relieved pains after a short time and led to a remarkably prompt healing. Its mechanism of action consists in the fact that it is capable of repairing local deficiencies in the oxygen metabolism of cells and of promoting to a great extent regeneration of tissues.

VII. Clinical Study of Treatment of Cardica Infarcts 210 cases of cardiac infarct were studied. 100 patients received conventional treatment and 110 patients received conventional treatment and 4 ml daily of blood extract produced by the process of example V. The results are summarized in Table IV. The blood extract was applied to the patients by the intravenous route.

Various modifications of the compositions and process of the invention may be made without departing from the spirit or scope therof and it is to be understood that the invention is intended to be limited only as defined in the appended claims.

We claim:
1. A process for the preparation of a tissue cell respiration stimulating blood extract which comprises (1) recovering the fresh blood of a calf, (2) defibrinating the said blood, (3) hemolyzing the defibrinated blood by stirring the latter with distilled water until hemolysis is complete, (4) removing the solids from the hemolyzed solution, (5) subjecting the resulting solution to dialysis with a cellophane membrane against an aqueous solution selected from the group consisting of distilled water and aqueous ethanol until substantially no nitrogen migrates to the dialysate, then concentrating and adjusting the pH of the outer dialysate to about 7.0 and (6) concentrating the said dialysate to a concentration of about 10 to 60 mg of dry components per ml of solution, and removing any inactive precipitate.
2. The process of claim 1 in which the calf has been subjected to stress by irradiation prior to recovering the fresh blood.
3. The process of claim 1 in which the calf has been subjected to stress by injection of a hypotonic aqueous solution prior to recovering the fresh blood.
4. A process for the preparation of tissue cell respiration stimulating blood extracts which comprises (1) recovering the fresh blood of a calf, (2) defibrinating the said blood by stirring at room temperature, (3) hemolyzing the defibrinated blood by stirring the latter with about an equal volume of distilled water until hemolysis is complete, (4) removing the solids from the hemolyzed solution, (5) subjecting the resulting solution to dialysis with a cellophane membrane against an aqueous solution selected from the group consisting of distilled water and aqueous ethanol until substantially no nitrogen migrates to the dialysate, then concentrating and adjusting the pH of the outer dialysate to about 7.0 and (6) then further twice concentrating the said dialysate to a concentration of about 40 mg of dry

TABLE IV

| Grouping by pathological indices | Conventional Treatment | | | Conventional Treatment and Blood Extract Treatment | | |
|---|---|---|---|---|---|---|
| | No. of Cases | No. of Deaths | % Mortality | No. of Cases | No. of Deaths | % Mortality |
| 0 – 25 | 22 | — | — | 10 | — | — |
| 26 – 50 | 21 | 1 | 4.7 | 37 | — | — |
| 51 – 75 | 25 | 8 | 32.0 | 24 | 1 | 4.1 |
| 76 – 100 | 14 | 10 | 71.4 | 21 | 3 | 14.3 |
| 100 – | 10 | 8 | 80.0 | 11 | 9 | 81.7 |
| Totals | 92 | 27 | 29.3 | 103 | 13 | 12.6 |
| 24 hour deaths | | 8 | | | 7 | |

In the control group the mortality rate was 29.3 percent as compared to the mortality rate of 12.6 percent in the group receiving the blood extract which is a significant statistical difference. It should be noted that among the milder cases and the most grave cases that no improvement of the results was recorded. However, among the cases of medium gravity, the difference in mortality rates was especially striking.

components per ml of solution, and removing any inactive precipitate.
5. The product produced by the process of claim 1.
6. The product produced by the process of claim 2.
7. The product produced by the process of claim 3.
8. The product produced by the process of claim 4.

* * * * *